United States Patent [19]

Amato et al.

[11] Patent Number: 5,420,260
[45] Date of Patent: May 30, 1995

[54] PROCESS FOR 4″-EPI-ACETYLAMINO-4″-DEOXY-5-OXIMINOAVERMECTIN $B_1$

[75] Inventors: Joseph S. Amato, Brooklyn, N.Y.; Raymond Cvetovich, Scotch Plains, N.J.

[73] Assignee: Merck & Co., Inc., Rahway, N.J.

[21] Appl. No.: 129,219

[22] Filed: Sep. 29, 1993

[51] Int. Cl.$^6$ .................. C07H 17/08; A01N 43/04
[52] U.S. Cl. ............................ 536/7.1; 549/264
[58] Field of Search ............... 536/7.1; 514/30, 450, 514/28; 549/264

[56] References Cited

U.S. PATENT DOCUMENTS

| 4,427,663 | 1/1984 | Mrozik | 424/180 |
| 5,015,630 | 5/1991 | Fisher et al. | 514/30 |
| 5,023,241 | 6/1991 | Linn et al. | 514/30 |

FOREIGN PATENT DOCUMENTS 0379341 1/1990 European Pat. Off. .
0411897 7/1990 European Pat. Off. .
0519731 6/1992 European Pat. Off. .

OTHER PUBLICATIONS

Ag. & Biol. Chem., vol. 55, No. 10, pp. 2615–2621 (1991), by Tsukamoto, et al.
C. R. Acad. Sc. Paris, t. 270 (12 Janvier 1970), pp. 240–242, by Frainnet, et al.

Primary Examiner—Douglas W. Robinson
Assistant Examiner—Howard C. Lee
Attorney, Agent, or Firm—Mollie M. Yang; David L. Rose

[57] ABSTRACT

An improved process for formation of a 5-oxime on avermectin derivatives comprises the treatment of the oxo-compound with hydroxylamine in aqueous isopropanol at pH 1.8–2.1.

1 Claim, No Drawings

PROCESS FOR 4"-EPI-ACETYLAMINO-4"-DEOXY-5-OXIMINOAVERMECTIN B₁

BACKGROUND OF THE INVENTION

The avermectins are a unique collection of naturally occurring macrocyclic lactones containing an α-L-oleandrosyl-α-L-oleandrose disaccharide appended to the $C_{13}$-hydroxyl group of the aglycone unit, and exhibit anthelmintic and insecticidal properties. Since the introduction and expanded use of 'abamectin' for the control of a variety of agricultural pests and the subsequent commercialization of 'ivermectin' in the animal health area including the use of 'MECTIZAN' for the control of riverblindness in humans a large number of avermectin derivatives have been synthesized seeking potential increases in the spectrum of parasite control in plants, animals and humans. Among these new analogues is 4"-epi-acetylamino-4"-deoxy-5-oximinoavermectin $B_1$. This derivative has attracted attention for the control of internal parasites in companion animals and its efficient preparation in large quantity is commercially important. This compound is described in U.S. Pat. Nos. 5,015,630 and 5,023,241 being prepared by treatment of the 5-oxo compound with hydroxylamine in the presence of base which produced mainly the 3-hydroxylamino-5-oximino analog as a by-product.

SUMMARY OF THE INVENTION

This invention is concerned with an improved process for the preparation of 5-oximinoavermectin $B_1$ analogs, particularly 4"-epi-acetylamino-4"-deoxy-5-oximinoavermectin $B_1$. The process comprises the treatment of the corresponding 5-oxo starting material with hydroxylamine hydrochloride in a controlled acidic environment.

These conditions provide yields of about 90% with minimal hydrolysis of the terminal saccharide and minimal production of a 3-hydroxylamino by-product formed by addition of hydroxylamine across the 3,4 double bond.

DETAILED DESCRIPTION OF THE INVENTION

The novel process of this invention comprises the preparation of the compound of structural formula I:

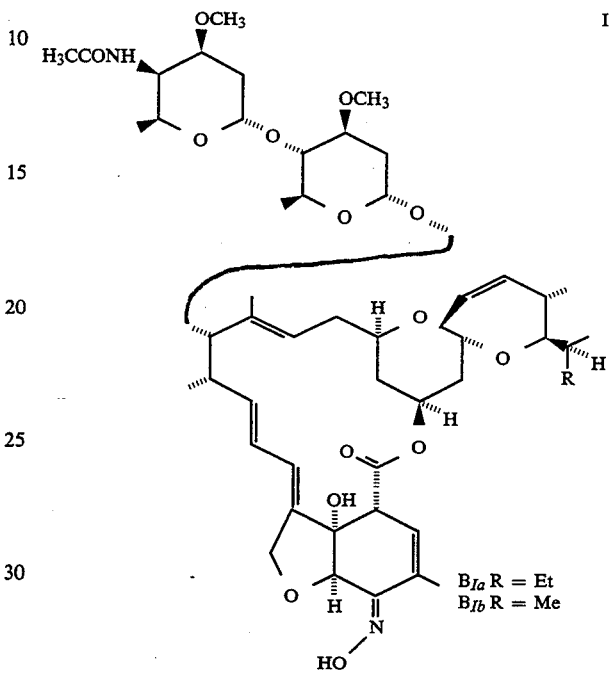

$B_{Ia}$ R = Et
$B_{Ib}$ R = Me by treating the compound of structural formula III:

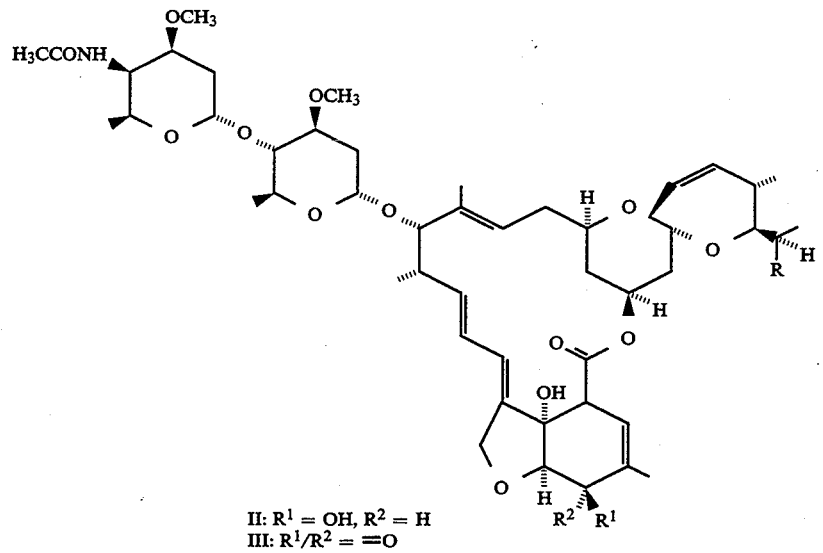

II: $R^1$ = OH, $R^2$ = H
III: $R^1/R^2$ = =O in isopropanol (IPA) with aqueous hydroxylamine hydrochloride at about pH 1.8–2.1 for about 8–12 hours.

The concentration of III in the IPA is not critical but is usually about 15–25 ml of IPA/gm of III. Similarly with the aqueous hydroxylamine, the concentration is not critical but concentrations of about 1 g of hydroxylamine hydrochloride per 20-35 ml of water are appropriate. An 8-10 molar excess of hydroxylamine hydrochloride is employed in the novel process.

The temperature at which the process is conducted also is not critical but temperatures of about 15° to 30° C. are appropriate; room temperature being most convenient.

Oximation of enone III was expected to result from the usual conditions of hydroxylamine hydrochloride in the presence of base. Oximation of III by the action of hydroxylamine hydrochloride in the presence of pyridine or diisopropyl ethylamine led to poor yields (30-60%) of oxime I. The major by-product found from these reactions was the 3-hydroxylamino-5-oxime (IV).

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, and poultry. Among the helminths the group of worms described as nematodes causes widespread and oftentimes serious infection in various species of animals. The most common genera of nematodes infecting the animals referred to above are Haemonchus, Trichostrongylus, Ostertagia, Nematodirus, Cooperia, Ascaris, Bunostomum, Oesophagostomun, Chabertia, Trichuris, Strongylus, Trichonema, Dictocaulus, Capillaria, Heterakis, Toxocara, Ascaridia, Oxyuris, Ancylostoma, Uncinaria, Toxascaris, and Parascaris.

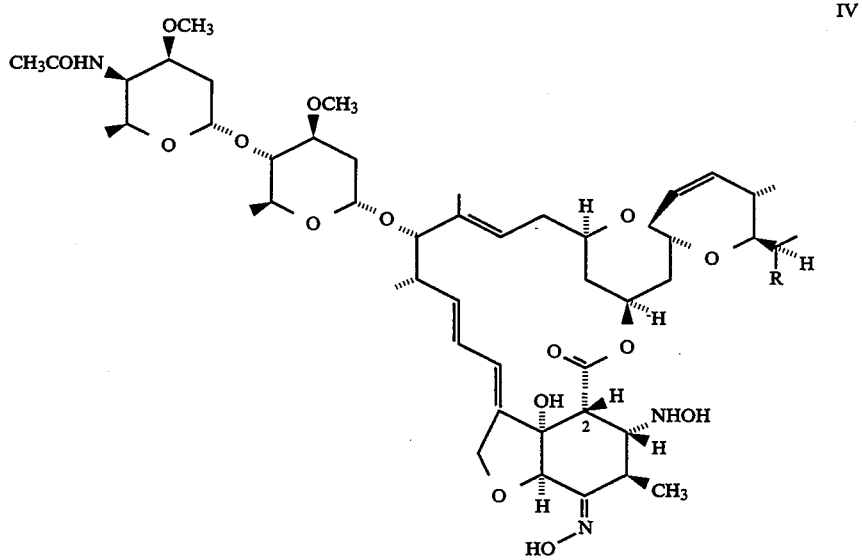

IV

The addition of hydroxylamine hydrochloride to ketone III in aqueous ethanol gave a 70% yield of oxime I. The greatest loss of yield resulted from hydrolytic removal of the terminal saccharide unit and the by-products of this process were difficult to remove during the crystallization of I. Monitoring the pH of the reaction mixture showed a continuous drop from pH=2.5 to <1 as the reaction progressed. When oximation reactions were performed at pH ranges of 3-7 using various buffered systems poor control of 1,4-hydroxylamine addition vs oxime formation resulted. When the reaction medium was changed from aqueous ethanol to aqueous isopropyl alcohol, and the pH was monitored and continuously adjusted to pH=1.8-2.2 with the addition of aqueous sodium bicarbonate, the formation of hydroxylamino-oxime by-product as well as the hydrolytic by-products were greatly minimized and a 90% yield of oxime I was attained. This mixture could then be crystallized from ethanol/water in >95 area % purity by HPLC analysis.

NMR experiments (NOE) have determined that the major stereochemical orientation of the oxime is as the Z- isomer, 1-Z.

The compound of this invention has significant parasiticidal activity as an anthelmintic, ectoparasiticide, insecticide, and acaracide, in human and animal health and in agriculture.

Certain of these, such as Nematodirus, Cooperia, and Oesophagostomum attack primarily the intestinal tract while others, such as Haemonchus and Ostertagia, are more prevalent in the stomach while still others such as Dictocaulus are found in the lungs. Still other parasites may be located in other tissues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in the death of the infected host. The avermectin compound of this invention has unexpected high activity against Dirofilaria in dogs, Nematospiroides, Syphacia, Aspiculuris in rodents, anthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

This compound may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 5% by weight of the active compound. Preferred drench formulations may contain from 0.001 to 0.1% by weight active compound. The capsules or boluses are comprised of the active ingredient admixed with a carrier vehicle such as starch, talc, magnesium stearate, or di-calcium phosphate.

Where it is desired to administer the avermectin derivative in a dry, solid unit dosage form, capsules, boluses, or tablets containing the desired amount of active compound usually are employed. The dosage forms are prepared by intimately and uniformly mixing the active ingredients with suitable finely divided diluents, fillers, disintegrating agents, and/or binders such as starch, lactose, talc, magnesium stearate, vegetable gums and the like. Such unit dosage formulations may be varied widely with respect to their total weight and content of antiparasitic agent depending upon factors such as the type of host animal to be treated, the severity and type of the infection and the weight of the host.

When the active compound is to be administered via the animal feedstuff, it is intimately dispersed in the feed or used as a top dressing or in the form of pellets which may then be added to the finished feed or optionally fed separately. Alternatively, the antiparasitic compound of this invention may be administered to the animals parenterally, for example, by intraruminal, intramuscular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil, and the like. Other parenteral vehicles such as organic preparations using solketal, glycerol formal, and aqueous parenteral formulations are also used. The active avermectin compound is dissolved or suspended in the parenteral formulation for administration; such formulations generally contain from 0.005 to 5% by weight of the active compound. The optimum amount to be employed will, of course, depend upon the species of animal to be treated and the type and severity of parasitic infection or infestation. Generally good results are obtained with this compound by the oral administration of from about 0.001 to 10 mg per kg of animal body weight, such total dose being given at one time or in divided doses over a relatively short period of time such as 1–5 days. Generally, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field. When the compound described herein is administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes: or supplements in which the active ingredient is present in relatively large amounts and which are suitable for the direct feeding to the animal or for addition to the feed either directly or after an intermediate dilution or blending step. Typical carriers or diluents suitable for such compositions include, for example, distillers' dried grains, cornmeal, citrus meal, fermentation residues, ground oyster shells, wheat shorts, molasses solubles, corncob meal, edible bean mill feed, soya grits, crushed limestone and the like. The active avermectin compound is intimately dispersed throughout the carrier by methods such as grinding, stirring, milling, or tumbling. Compositions containing from about 0.005 to 2.0% weight of the active compound are particularly suitable as feed premixes. Feed supplements, which are fed directly to the animal, contain from about 0.002 to 0.3% by weight of the active compounds.

Such supplements are added to the animal feed in an amount to give the finished feed the concentration of active compound desired for the treatment and control of parasitic diseases. Although the desired concentration of the active compound will vary depending upon the factors previously mentioned as well as upon the particular avermectin derivative employed, the compound of this invention is usually fed at concentrations of between 0.00001 to 0.002% in the feed in order to achieve the desired antiparasitic result.

EXPERIMENTAL

General. HPLC analyses were performed using a Spectra-Physics SP8700 ternary solvent delivery system with a Vydac C18 Protein/Peptide (218TP54) reverse phase column, at 25° C., UV detection at 245 nm, with the solvent systems described in each experimental. All reactions were carried out under an atmosphere of $N_2$, and the solvents and reagents were used as received or were dried over 3 Å molecular sieves prior to use as needed. Karl Fisher water analyses were performed with a Metrohm 684 KF Coulometer, Infrared spectra were recorded on a Perkin-Elmer 1420 Ratio Recording Infrared Spectrophotometer. Melting points were determined using a DuPont 9900 SDC (2° C./min, under $N_2$ in an open up) and are reported as a range from the DSC extrapolated onset temperature to the peak temperature. 1H and $^{13}$C NMR spectra were recorded in $CDCl_3$ on a Bruker AM-400 at a frequency of 400.13 and 100.16 MHz, resp. The chemical shifts are reported in ppm relative to residual $CHCl_3$ for proton ($\delta=7.27$ ppm) and $CDCl_3$ for carbon ($\delta=77.0$ ppm). All coupling constants are reported in Hz and the following proton multiplicites are abbreviated as follows: s=singlet, d=doublet, t=triplet, q=quartet, m=multiplet, om=overlapping multiplets, br=broad. High resolution mass spectroscopy studies were performed in the FAB mode.

EXAMPLE 1

4″-Epi-Acetylamino-4″-Deoxy-5-oximino-avermectin $B_1$

Step A: Preparation of 4″-Epi-Acetylamino-4″-Deoxy-5-Oxo-avermectin $B_1$

To a solution of 4″-epi-acetylamino-4″-deoxyavermectin $B_1$ (25.0 g, 25.8 mmol), DMSO (7.5 mL) and triethylamine (18.5 mL) in iPrOAc (175 mL) at −20° C. was added phenyl dichlorophosphate (7.55 mL) over 30 min. After a 90 min age at −10° C., the reaction was quenched with sat aq NaCl (100 mL), and the organic phase was washed with a 1:1 mixture of sat aq $NaHCO_3$ and sat aq NaCl (100 mL). The solvent was removed in vacuo (40° C., 28 in Hg) to give a solid foam (24.6 g) which was used as is for the oximation steps. A sample was is purified by silica gel chromatography (E. Merck Silica Gel 60, 230–400 mesh, 25% ethyl acetate/hexanes). HPLC assay: gradient, acetonitrile:water (0.1% $H_3PO_4$), 50:50 to 90:10 over 30 min; (II) $t_R$: $B_{1b}$=5.18 min, $B_{1a}$=6.86 min; (III) $t_R$: $B_{1b}$=10.3 min, $B_{1a}$=12.4 min.

$^1$H NMR: δ6.58 (br s, $H_3$), 5.93 (d, J=10.3, $H_9$), 5.82–5.69 (om, $H_{10}$, $H_{11}$, $H_{23}$), 5.60 (d, J=10.0, NH), 5.66 (d, J=9.9, 4″-NH), 5.56 (dd, J=2.5, 9.9, $H_{22}$) 5.42 (m, $H_{19}$), 5.38 (d, J=3.8, $H_{1″}$), 4.98 (m, $H_{15}$), 4.78 (br d, J=3.1, $H_{1′}$), 4.73 (m, $C_{8a}H_2$), 4.44 (dd, J=10.0, 2.9, $H_{4″}$), 4.10–3.98 (om, $H_{5″}$, 7-OH), 3.94 (br s, $H_{13}$), 3.93–3.77 (om, $H_{17}$, $H_{5′}$), 3.85 (s, $H_6$), 3.71–3.54 (m, $H_{3″}$, $H_{3′}$), 3.59 (m, $H_2$), 3.48 (br d, 9.5, $H_{25}$), 3.43, 3.39 (s,s, 3′-OCH$_3$, 3″-OCH$_3$), 3.21 (t, J=9.0, $H_{4′}$), 2.53 (m, $H_{12}$), 2.37–2.18 (om, $C_{16}H_2$, $H_{24}$, $C_2$,$H_{eq}$), 2.06 (s, COCH$_3$), 2.03 (om, $C_{20}H_{eq}$, $C_{2″}H_{eq}$), 1.88 (s, $C_{4a}H_3$), 1.80 (m, $C_{18}H_{eq}$), 1.67–1.41 (om, $C_{20}H_{ax}$, $H_{26}$, $C_{27}H_2$, $C_2$, $H_{ax}$, $C_{2″}H_{ax}$), 1.49 (br s, $C_{14a}H_3$), 1.23 (d, J=6.2, $C_6$′$H_3$), 1.16 (d, J=6.7 $C_{12a}H_3$), 1.13 (d, J=6.5 $C_{6″}H_3$), 0.98–0.89 (om, $C_{18}H_{ax}$, $C_{24a}H_3$, $C_{26a}H_3$, $C_{28}H_3$). $^{13}$C NMR: δ192.1 ($C_5$), 172.2 ($C_1$), 170.8 (CH$_3$CO), 139.0 ($C_{11}$), 138.1 ($C_3$), 137.9 ($C_8$), 136.8 ($C_4$), 136.4 ($C_{22}$), 135.2 ($C_{14}$), 127.5 ($C_{23}$), 124.6 ($C_{10}$), 121.8 ($C_9$), 118.1 ($C_{15}$), 98.7 ($C_{1″}$), 95.8 ($C_{21}$), 94.9 ($C_{1′}$), 82.0 ($C_{13}$), 81.9 ($C_7$), 81.0 ($C_{4′}$), 80.8 ($C_6$), 79.3 ($C_{3′}$), 74.9 ($C_{25}$), 73.3 ($C_{3″}$), 69.9 ($C_{8a}$), 69.1 ($C_{19}$), 68.4 ($C_{5′}$), 67.1 ($C_{17}$), 65.5 ($C_{5″}$), 56.4 (3′-OCH$_3$), 55.9 (3″-OCH$_3$), 48.4 ($C_{4″}$), 46.6 ($C_2$), 40.5 ($C_{20}$), 39.9 ($C_{12}$), 36.6 ($C_{18}$), 35.2 ($C_{26}$), 34.5 ($C_{16}$), 34.2 ($C_{2′}$), 31.9 ($C_{2″}$), 30.6 ($C_{24}$), 27.6 ($C_{27}$), 23.5 (CH$_3$CO), 20.1 ($C_{12a}$), 18.3 ($C_{6′}$), 17.1 ($C_{6″}$), 16.4 ($C_{24a}$), 15.5 ($C_{4a}$), 15.1 ($C_{14a}$), 13.0 ($C_{26a}$), 12.1 ($C_{28}$). HRMS: [MH]$^+$=912.5087 (Calculated=912.5108). IR (CCl$_4$): $\lambda_{max}$=3440, 2980, 2940, 1735, 1712, 1685, 1500, 1450, 1370, 1120, 980 cm$^{-1}$. Anal. Calcd for $C_{50}H_{73}NO_{14}$: C, 65.84; H, 8.07; N, 1.54. Found: C, 65.85; H, 8.30; N, 1.90.

Step B: Preparation of 4″-Epi-Acetylamino-4″-Deoxy-5-oximino-avermectin $B_1$

Ketone from Step A (21.6 g, 23.7 mmol) was dissolved in IPA (400 mL) and a solution of hydroxylamine hydrochloride (15.0 g, 220 mmol) in water (40 mL) was added. The pH of the solution was maintained at 1.8–2.1 by the addition of sat aq NaHCO$_3$ via a syringe pump controlled by a Cole-Parmer Chemcadet ® pH meter/controller during a 10 h reaction age. After a final adjustment to pH=4, the mixture was diluted with MTBE (500 mL) and H$_2$O (500 mL). The organic phase was washed with H$_2$O (2×250 mL), concentrated in vacuo (25° C., 25 in Hg) and dissolved in EtOH (170 mL). The solution was warmed to 60° C., H$_2$O (75 mL) was added and the product crystallized upon cooling. The slurry was cooled to 0° C., filtered, washed (2:1 ethanol:water), and dried to give I (18.5 g, 82% yield), m.p. =185°–91° C. HPLC assay: gradient, acetonitrile:water (0.1% H$_3$PO$_4$), 50:50 to 88:12 over 15 min, 2.0 mL/min; (IV) $B_{1b}$: $t_R$=4.0 min, $B_{1a}$:$t_R$=4.76 min; (Ia) $B_{1b}$:$t_R$=7.95 min, $B_{1a}$:$t_R$=9.38 min; (Ib) $B_{1a}$:$t_R$=9.68 min; (III) $B_{1b}$:$t_R$=9.41 min, $B_{1a}$:$t_R$=10.89 min. $^1$H NMR: δ8.93 (br, N-OH), 5.94 (m, $H_9$), 5.81 (m, $H_3$), 5.77 (dd, J=9.9, 1.6; $H_{23}$), 5.75 (om, $H_{10}$, $H_{11}$), 5.66 (d, J=9.9, NH), 5.56 (dd, J=9.9, 2.8, $H_{22}$), 5.44 (m, $H_{19}$), 5.39 (d, J=4.0, $H_{1″}$), 4.98 (br dd, J=9.5, 4.8, H 15), 4.80–4.66 (om, $C_{8a}H_2$, $H_{1′}$), 4.67 (s, $H_6$), 4.44 (dd, J=10.3, 3.6, $H_{4″}$), 4.07 (qd, J=6.3, 1.2, $H_{5″}$), 3.94 (br s, $H_{13}$), 3.87 (om, 7-OH, $H_{17}$, $H_{5′}$), 3.70 (m, $H_{3′}$), 3.63 (ddd, J=11.5, 8.7, 4.8, $H_{3′}$), 3.49 (dd, 9.9, 1.2, $H_{25}$), 3.44 (s, 3′-OCH$_3$), 3.42 (m, $H_2$), 3.40 (s, 3″-OCH$_3$), 3.22 (t, J=9.1, $H_{4′}$), 2.53 (m, $H_{12}$), 2.35–2.20 (om, $C_{16}H_2$, $H_{24}$, $C_2$·$H_{eq}$), 2.07 (s, COCH$_3$), 2.03 (om, $C_{20}H_{eq}$, $C_{2″}H_{eq}$), 1.94 (dd, J=2.4, 1.2, $C_{4a}H_3$), 1.80 (m, $C_{18}H_{eq}$), 1.67–1.44 (om, $C_{20}H_{ax}$, $H_{26}$, $C_{27}H_2$, $C_2$·$H_{ax}$, $C_{2″}H_{ax}$), 1.50 (br s, $C_{14a}H_3$), 1.24 (d, J=6.3, $C_{6′}H_3$), 1.17 (d, J=6.7, $C_{12a}H_3$), 1.13 (d, J=6.3, $C_{6″}H_3$), 0.98–0.89 (om, $C_{24a}H_3$, $C_{26a}H_{3l}$, $C_{28}H_3$), 0.89 (om, $C_{18}H_{ax}$). $^{13}$C NMR: δ173.2 ($C_1$), 170.9 (CH$_3$CO), 151.4 ($C_5$), 138.2 ($C_8$), 138.1 ($C_{11}$), 136.3 ($C_{23}$), 135.1 ($C_{14}$), 132.2 ($C_4$), 127.7 ($C_{22}$), 125.0 ($C_3$), 124.9 ($C_{10}$), 121.3 ($C_9$), 118.3 ($C_{15}$), 98.7 ($C_{1″}$), 95.8 ($C_{21}$), 94.9 ($C_{1′}$), 82.0 ($C_{13}$), 81.1 ($C_{4′}$), 79.3 ($C_{3′}$), 78.6 ($C_7$), 74.9 ($C_{25}$), 73.3 ($C_{3″}$), 72.9 ($C_6$), 68.7 ($C_{8a}$), 68.5, 68.4 ($C_{17}$, $C_{19}$), 67.0 ($C_{5′}$), 65.5 ($C_{5″}$), 56.6 (3′-OMe), 56.1 (3′-OMe), 48.4 ($C_{4″}$), 46.4 ($C_2$), 40.5 ($C_{20}$), 39.9 ($C_{12}$), 36.6 ($C_{18}$), 35.2 ($C_{26}$), 34.5 ($C_{2′}$), 34.2 ($C_{16}$), 31.8 ($C_{2″}$), 30.6 ($C_{24}$), 27.5 ($C_{27}$), 23.4 (CH$_3$CO), 20.2 ($C_{12a}$), 18.3 ($C_{6′}$), 17.5 ($C_{4a}$), 17.0 ($C_{6″}$), 16.4 ($C_{24a}$), 15.1 ($C_{14a}$), 13.0 ($C_{26a}$), 12.0 ($C_{28}$). HRMS: [M+Li]$^+$=933.5315 (calculated =933.5299). IR (CHCl$_3$): $\lambda_{max}$=3660, 3450, 3010, 2990, 2940, 1710, 1665, 1505, 1450, 1370, 1340, 1190, 1120, 1050, 990 cm$^{-1}$. Anal. Calcd for $C_{50}H_{74}N_2O_{14}$ and corrected for 5.8 wt % EtOH and 3.92 wt % H$_2$O: C, 62.0; H, 8.21; N, 2.81. Found: C, 61.7; H, 8.55; N, 2.79.

What is claimed is:

1. A process for the preparation of the compound of structural formula I.

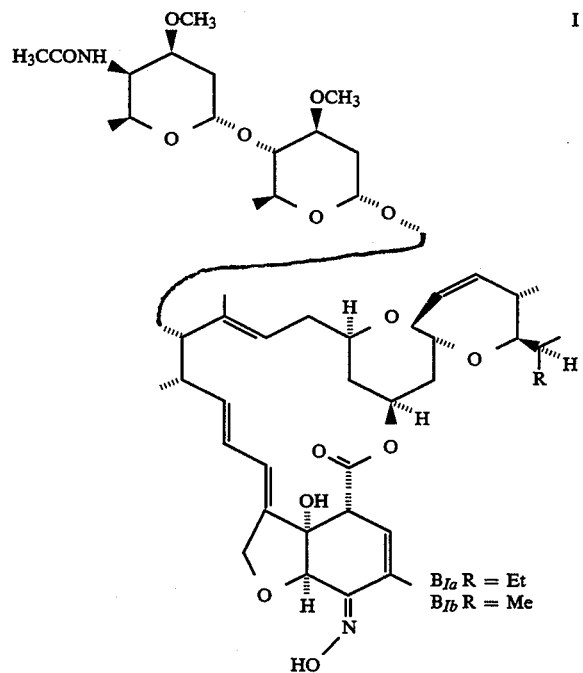

$B_{Ia}$ R = Et
$B_{Ib}$ R = Me which comprises the treatment of the compound of formula III

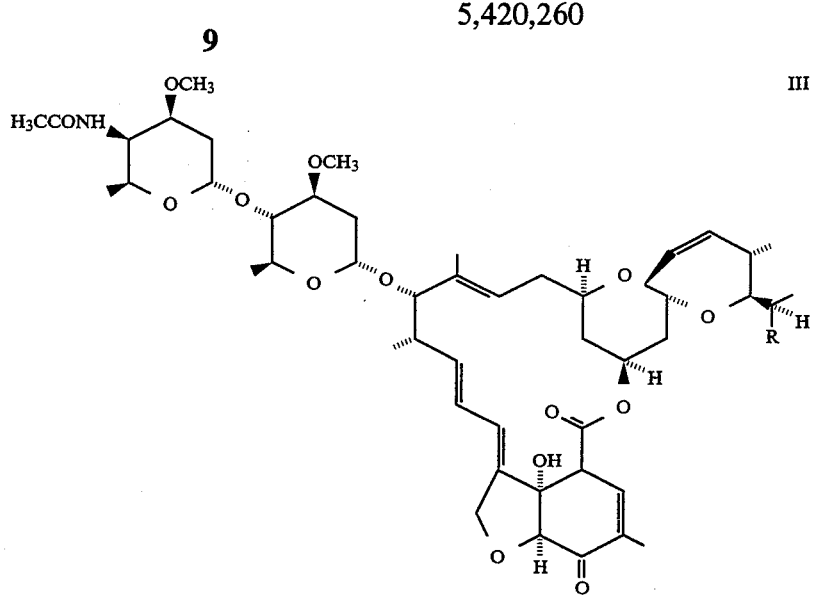
III
in isopropanol width aqueous hydroxylamine hydrochloride while controlling the pH at about 1.8–2.1 with sodium bicarbonate for about 8–12 hours.
* * * * *

UNITED STATES PATENT AND TRADEMARK OFFICE
CERTIFICATE OF CORRECTION

PATENT NO. : 5,420,260

DATED : May 30, 1995

INVENTOR(S) : Joseph S. Amato et al

It is certified that error appears in the above-indentified patent and that said Letters Patent is hereby corrected as shown below:

Column 2 between lines 8 and 34, delete the structural formula and replace it with the following:

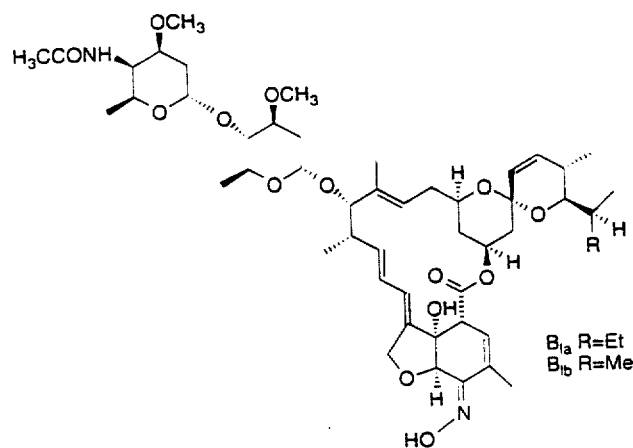

UNITED STATES PATENT AND TRADEMARK OFFICE
CERTIFICATE OF CORRECTION

PATENT NO. : 5,420,260　　　　　　　　　　　　　Page 2 of 5
DATED : May 30, 1995
INVENTOR(S) : Joseph S. Amato et al It is certified that error appears in the above-indentified patent and that said Letters Patent is hereby corrected as shown below:

Column 2, between lines 36 and 60, delete the structural formula and replace it with the following:

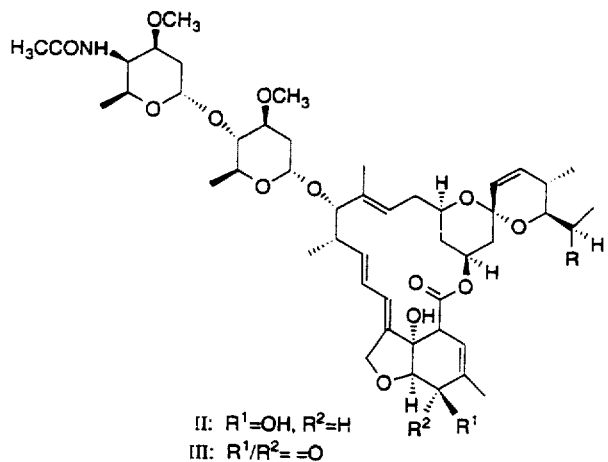

II: $R^1$=OH, $R^2$=H
III: $R^1/R^2$= =O

UNITED STATES PATENT AND TRADEMARK OFFICE
CERTIFICATE OF CORRECTION

PATENT NO. : 5,420,260    Page 3 of 5
DATED : May 30, 1995
INVENTOR(S) : Joseph S. Amato et al It is certified that error appears in the above-indentified patent and that said Letters Patent is hereby corrected as shown below:

Columns 3 and 4, between lines 16 and 40, delete the structural formula and replace it with the following:

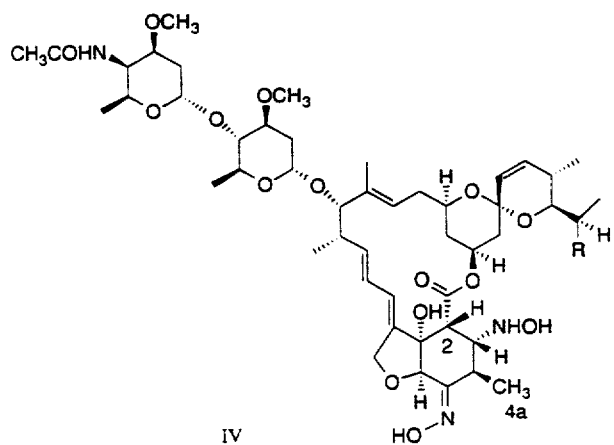

UNITED STATES PATENT AND TRADEMARK OFFICE
CERTIFICATE OF CORRECTION

PATENT NO. : 5,420,260
DATED : May 30, 1995
INVENTOR(S) : Joseph S. Amato et al

It is certified that error appears in the above-indentified patent and that said Letters Patent is hereby corrected as shown below:

In claim 1, column 8 between lines 35 and 64, delete the structural formula and replace it with the following:

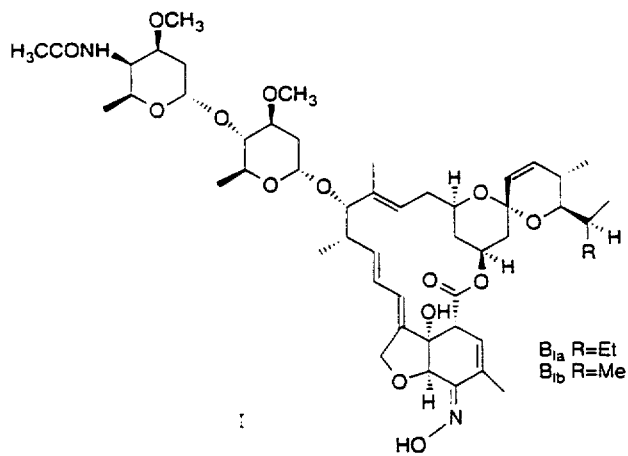

UNITED STATES PATENT AND TRADEMARK OFFICE
CERTIFICATE OF CORRECTION

PATENT NO. : 5,420,260  
DATED : May 30, 1995  
INVENTOR(S) : Joseph S. Amato et al Page 5 of 5

It is certified that error appears in the above-indentified patent and that said Letters Patent is hereby corrected as shown below:

In claim 1, columns 9 and 10 between lines 1 and 20, delete the structural formula and replace it with the following:

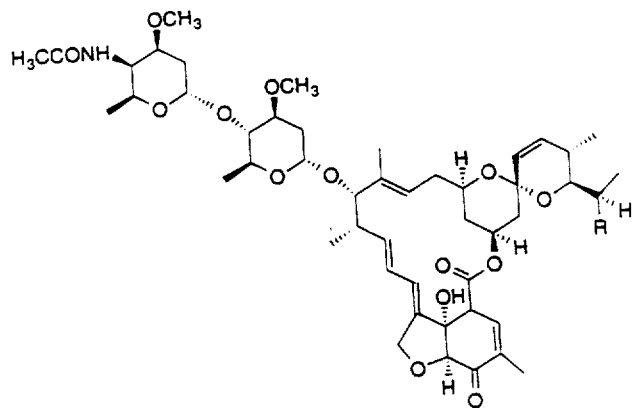

III

Signed and Sealed this

Seventeenth Day of October, 1995

Attest:

BRUCE LEHMAN

Attesting Officer

Commissioner of Patents and Trademarks